(12) United States Patent
Howling et al.

(10) Patent No.: US 8,980,425 B2
(45) Date of Patent: Mar. 17, 2015

(54) BIOACTIVE MATERIAL

(75) Inventors: Graeme Howling, Leeds (GB); Paul Gunning, York (GB)

(73) Assignee: Smith & Nephew PLC (GB)

( * ) Notice: Subject to any disclaimer, the term of this patent is extended or adjusted under 35 U.S.C. 154(b) by 491 days.

(21) Appl. No.: 12/674,236

(22) PCT Filed: Aug. 19, 2008

(86) PCT No.: PCT/GB2008/002814
§ 371 (c)(1),
(2), (4) Date: Nov. 12, 2010

(87) PCT Pub. No.: WO2009/024778
PCT Pub. Date: Feb. 26, 2009

(65) Prior Publication Data
US 2011/0059312 A1 Mar. 10, 2011

(30) Foreign Application Priority Data

Aug. 20, 2007 (GB) .................................. 0716220.9
Sep. 6, 2007 (GB) .................................. 0717317.2
Feb. 1, 2008 (GB) .................................. 081840.0
Jun. 19, 2008 (GB) .................................. 0811268.2

(51) Int. Cl.
| | | |
|---|---|---|
| B32B 15/04 | (2006.01) | |
| B32B 5/00 | (2006.01) | |
| B32B 5/16 | (2006.01) | |
| B05D 3/12 | (2006.01) | |
| B82Y 99/00 | (2011.01) | |
| A61L 24/04 | (2006.01) | |
| A61L 27/30 | (2006.01) | |
| C23C 22/64 | (2006.01) | |

(52) U.S. Cl.
CPC ............... *A61L 24/04* (2013.01); *A61L 27/306* (2013.01); *C23C 22/64* (2013.01); *Y10S 977/755* (2013.01)

USPC .......... 428/328; 428/472; 428/457; 428/336; 977/755

(58) Field of Classification Search
None
See application file for complete search history.

(56) References Cited

U.S. PATENT DOCUMENTS

| 5,609,633 | A | 3/1997 | Kokubo | |
|---|---|---|---|---|
| 7,857,244 | B2 * | 12/2010 | Yadav et al. | ..................... 241/23 |
| 7,892,599 | B2 * | 2/2011 | Yadav et al. | .................. 427/212 |
| 2003/0059742 | A1 | 3/2003 | Webster | |
| 2004/0146752 | A1 | 7/2004 | Axen et al. | |
| 2006/0078726 | A1 * | 4/2006 | Antonio et al. | ............... 428/328 |
| 2006/0229715 | A1 * | 10/2006 | Istephanous et al. | ......... 623/1.46 |

FOREIGN PATENT DOCUMENTS

| EP | 0678300 A1 | 10/1995 |
|---|---|---|
| JP | 08257109 | 10/1996 |

(Continued)

OTHER PUBLICATIONS

International Search Report in Application No. PCT/GB2008/002814.
Office Action dated Oct. 4, 2010 issued in related European Patent Application No. 08788378.1.
English language translation of Notice of Reasons for Rejection dated May 7, 2013 in Japanese Patent Application No. 2010-521471.

(Continued)

*Primary Examiner* — Vera Katz
(74) *Attorney, Agent, or Firm* — Kilpatrick Townsend & Stockton LLP

(57) ABSTRACT

The present invention relates to a bioactive material and to a method of producing a bioactive material which is suitable for use as an implant or for use as a bone substitute for repairing bone.

12 Claims, 21 Drawing Sheets

(56) References Cited

FOREIGN PATENT DOCUMENTS

| JP | 2775523 | | 7/1998 |
|---|---|---|---|
| JP | 2000210313 | * | 2/2000 |
| JP | 2000-210313 | | 8/2000 |
| JP | 2000210313 | | 8/2000 |
| WO | WO2006104644 | | 10/2006 |
| WO | WO2007040298 | | 4/2007 |

OTHER PUBLICATIONS

Office Action, Japanese Patent Application No. 2010-521471, mailed Jun. 2, 2014.
Human English Translation of JP 2000-210313 completed Jun. 25, 2014, machine translation previously cited in IDS dated Jul. 15, 2013, and Translator Certification executed Sep. 23, 2014.

* cited by examiner

BIOACTIVE MATERIAL

CROSS REFERENCE TO RELATED APPLICATIONS

This application is the U.S. national phase of International Application No. PCT/GB2008/002814 filed on Aug. 19, 2008 and published in English on Feb. 26, 2009 as International Publication No. WO 2009/024778 A2, which application claims priority to Great Britain Application No. 0716220.9 filed on Aug. 20, 2007, Great Britain Application No. 0717317.2 filed on Sep. 6, 2007, Great Britain Application No. 0801840.0 filed on Feb. 1, 2008, and Great Britain Application No. 0811268.2 filed on Jun. 19, 2008, the entire contents of all of which are incorporated herein by reference.

FIELD OF THE INVENTION

The present invention relates to a material and to a method of producing a material which is suitable for use as an implant or for use as a bone substitute for repairing bone.

BACKGROUND OF THE INVENTION

Restoration of skeletal defects or wounds such as femoral neck fracture, spine fusion and lost teeth is a common procedure. For example, over 500,000 hip prosthesis implantations, 250,000 spine fusion surgeries, and 500,000 dental implant surgeries are performed annually in the United States alone.

Titanium and its alloys, due to their high toughness and excellent biocompatibility, are widely used in medical implants such as joint prostheses, fracture fixation devices, and dental implants. Other materials commonly used in medical and dental implants, include cobalt chrome, polished zirconium, oxinium (zirconium oxide) and stainless steel. However, titanium and these other materials demonstrate poor ability to bond to bone chemically, and thus osteolysis and subsequent loosening of implants comprising these materials are common.

The performance of an orthopaedic implant can be influenced by the quality of the interface formed between the implant and bone or bone cement. The development of the implant-to-bone (or cement) interface relies on a number of factors including surface area, charge, topography, chemistry and contamination of the implant. The implant-to-bone interface is the surface of the implant which interfaces or lies adjacent the bone when implanted.

Various techniques are known to modify the implant-to-bone interface topography to enhance implant-to-bone integration. These techniques include plasma spraying and electrochemical anodising of the implant-to-bone interface surface. Problems associated with plasma spraying and electrochemical anodising include, the formation of an implant-to-bone interface which has low fatigue strength, demonstrates poor adherence to the implant, and suffers from degradation, delamination or cracking during long term implantation.

A commonly used technique for improving tissue ingrowth into orthopaedic implants is abrasive particle blasting of the implant surface, alternatively known as grit-blasting or sand blasting. This cost efficient process, imparts a micron scale surface structure by blasting abrasive particles on the implant surface. Such roughened surfaces have been shown to promote cell attachment and thus improved physical implant-to-bone bonding. Furthermore, the increased area of a roughened surface means that more cells can attach to the implant-to-bone interface which also improves implant-to-bone physical bonding. The implant having such a modified implant-to-bone interface demonstrates good osseointegrative properties even in poor quality bone.

However the technique of abrasive particle blasting can cause significant changes to surface topography by damaging the metal elements on the surface of the implant. The technique of abrasive particle blasting can also cause heterogeneity of the surface chemistry due to the presence of abrasive particles embedded in the surface of the implant. The presence of the abrasive particles contaminate the surface of the implant and adversely affect the quality of the implant-to-bone interface. Furthermore, the abrasive particles can detach from the surface of the implant, leading to increased wear on the bone, implant and implant site.

Additionally, a percentage of the embedded abrasive particles protrude from the surface of the implant causing localised micromotion, movement of the implant relative to the implant site, and disruption of tissue ingrowth in the surface of the implant. Up to 40% of the surface area of the grit blasted implant can become contaminated with abrasive particles which can lead to implant-to-bone interface problems, reduced bio-compatibility of the implant and inflammation of the area local to the implant.

SUMMARY

It is the object of the present invention to provide an implant which has an enlarged implant-to-bone interface layer with reduced or no contamination caused by surface embedded abrasive particles. The implant-to-bone interface is the surface of the implant which interfaces or lies adjacent the bone when implanted. It is also an object of the present invention to provide an implant which has a bioactive, porous and nano-structured surface layer with improved osteoconductive and osteoinductive properties.

Therefore, according to a first aspect of the invention, there is provided a material suitable as an implant comprising a metal or metal alloy substrate and a primary layer formed on a surface of the substrate, said primary layer having a surface area greater than the surface area of the substrate. Surprisingly it has been found that the primary layer according to the present invention, having a surface area greater than the surface area of the substrate, encourages (to a greater extent) bone to be formed on the surface. Thus increasing bone formation and giving a secure hold on the implant, giving a greater implant success rate both in terms of speed to recover from the implant operation and overall success of the implant being secured in place.

In use, the surface of the primary layer of the implant interfaces the bone or bone cement. Thus, the primary layer, or more specifically, the surface of the primary layer provides the implant-to-bone interface. The increased surface area of the primary layer means that a larger surface area is presented to surrounding cells/cement for increased cell/cement attachment and hence improved integration with the material and thus with the implant.

According to a second aspect of the invention, there is provided a method of forming the material of the first aspect, comprising the steps of providing a metal or metal alloy substrate and forming a primary layer on a surface of the substrate such that the surface area of the primary layer is greater than the surface area of the substrate covered by the primary layer.

Preferably, the substrate comprises a transition metal, a transition metal alloy or a transition metal oxide, for example, titanium, TiAlNb, or titanium oxide. Titanium and its alloys, due to their high toughness and excellent biocompatibility are ideally suited as orthopaedic implants. Optionally, the substrate may comprise cobalt chrome, polished zirconium, oxinium (zirconium oxide), stainless steel, tantalum or any combination of these. The substrate according to the present invention may comprise any metal, or metal alloy, or metal oxide or combination of these but suitably it would comprise titanium.

Preferably, the step of forming the primary layer on the metal substrate comprises physically altering the surface of the substrate. Physically altering the surface of the substrate roughens the surface of the substrate thereby increasing its surface area. The primary or rough layer promotes cell attachment and thus physical bonding of the implant to bone or to the implant site. The roughened surface presented by the primary layer provides a surface area significantly larger than the surface area of the substrate covered by the primary layer.

The step of physically altering the surface of the substrate to form the primary layer may comprise, for example, machining, sand blasting or grit blasting, or any combination of these. Preferably, the physical altering step comprises grit blasting the surface of the substrate with abrasive particles such as alumina. The primary layer thus formed presents a roughened, uneven surface texture of peaks, troughs, pits and trenches which increases the surface area available for cell attachment.

Alternatively, the step of physically altering the substrate may comprise, for example, a macro or micro physical surface-treatment in which a coating of metallic beads is adhered to the surface of the substrate. The beads form a 3D porous geometry on the surface of the substrate thereby providing a primary layer having a greater surface area than the surface of the substrate covered by the coating. Preferably, the primary layer comprises a double or triple layer of beads sintered onto the surface of the substrate. Preferably, the beads are titanium beads and have a mean diameter of 328 µm.

Alternatively, or in addition, the coating may contain a sponge or foam like network of metallic fibres and/or wires. Alternatively, the substrate itself can be porous or sponge like, negating the requirement to physically treat the surface of the substrate. Preferably, the foam or sponge-like structure is composed of sintered beads having diameters of between 15 and 50 µm and pore diameters of several hundred microns to approximately 1 mm.

In addition, and subsequent to the physically formed primary layer, the method of forming or completing the primary layer ideally includes chemically treating the physically formed primary layer. The step of chemically treating the physically formed primary layer comprises soaking the substrate in an alkaline solution at approximately 30-90° C. The titanium or titanium alloy reacts with the alkaline solution to form alkali titanates. The surface of the completed primary layer thus comprises alkali titanates. Typically, the surface of the completed primary layer also includes titanium oxide or titanium oxides.

Preferably, the temperature of the alkaline solution is between 50-70° C. and more preferably between 55-65° C.

It has been found that to heat the substrate or alkaline solution to a higher temperature can compromise the integrity of the primary layer so formed. For example, where the substrate or alkaline solution is heated to or above 150° C., a primary layer having a deposit of alkali titanates of a thickness in the micron scale will form. The thicker the alkali titanate deposit or layer, the greater will be the risk of delamination or cracking of the alkali titanate layer. Thus the alkali titanate layer, which will in effect form the implant-to-bone interface, bonding the implant to the bone, may be weak and ultimately fail causing separation of the implant from the bone.

Preferably, the substrate is soaked in an alkaline solution for between 1 and 24 hours. Typically, the soaking time is between 1 and 5 hours but is preferably between 1 and 3 hours. It has been found that soaking times above 5 hours but in particular above 24 hours also produce a primary layer having a thickness in the micron scale.

The alkali titanate layer creates a surface to the primary layer which comprises a nanostructure of alkali titanates. A nanostructure or nano-textured surface generally means a surface which includes particles or elements of a size falling within the nanometer range. The nanostructure of alkali titanates resembles a strut-like morphology containing discrete elements, structurally resembling fibres or fibrils, of alkali titanate having a width of between 1 and 20 nanometers (nm). The fibrils are generally cylindrical in shape.

Typically, the length of the fibrils range from 200-300 nm and the distance between fibrils ranges from 5 nm to 80 nm. The fibrils are generally overlaid or stacked one atop another forming the alkali titanate layer or surface. Preferably, the thickness of the alkali titanate layer is in the range of 100-500 nanometers, more preferably 100-300 nanometers.

The physical treatment step creates the primary layer having an increased surface area in preparation for the formation of the alkali titanate nanostructure. The nanostructure of the alkali titanate layer completes the primary layer and significantly increases the surface area of the primary layer and hence implant-to-bone interface surface area available for cell attachment and integration. The alkali titanate layer also masks the adverse affects caused by the presence of any abrasive particles present in the implant-to-bone interface of the implant.

Preferably, the primary layer has a surface area of between 1000 and 50000 times greater than the surface area of the substrate covered by the primary layer. More preferably, the primary layer has a surface area of between 20000 and 50000 times and ideally between 40000 and 50000 times greater than the surface area of the substrate covered by the primary layer.

Typically, the alkaline solution comprises a hydroxide. Preferably, the hydroxide is sodium hydroxide. Other hydroxides can be used with the present invention, e.g. lithium hydroxide or potassium hydroxide or any other suitable metal hydroxide. In this case, the alkali titanate nanostructure of the primary layer will be sodium titanate. Sodium titanate is an ionic compound that can be readily modified by ion-exchange chemistry into other compounds such as lithium titanate or strontium titanate to confer different physico-chemical or biocompatibility characteristics suitable for different applications. The concentration of the hydroxide solution is preferably between 2 and 8 molar, more preferably between 3 and 6 molar, and ideally 4 molar. Higher concentrations of hydroxide can lead to re-dissolution of the nanostructure.

The primary layer formed is typically hydrophilic in nature. This is generally due to the chemical treatment step in completing the primary layer. The hydrophilic nature of a material is generally measured by the contact angle water forms on its surface. The smaller the contact angle the greater the hydrophilic nature of the material. Preferably, the contact angle of the primary layer is less than 5°, more preferably is less than 3°.

Preferably, the primary layer has a low reflectance to visible light. Typically, the primary layer has a reflectance to visible light in the range of 1% to 20%. More preferably the primary layer has a reflectance to visible light in the range of 5% to 15% and ideally in the range of 6% to 10%. The reflectance range gives the primary layer a black colour.

Preferably, the primary layer includes hydroxyapatite, for example calcium hydroxyapatite. Typically, the hydroxyapatite is incorporated in the primary layer by soaking the material in mixed buffer salts.

The material may be used in both medical and dental implants for improved implant-to-bone integration. More specifically, the material may be used in bone replacement implants including, for example, knee joint, hip joint and shoulder joint prosthesis, femoral neck replacement, spine replacement and repair, neck bone replacement and repair, jaw bone repair, fixation and augmentation, transplanted bone fixation, and other limb prosthesis.

BRIEF DESCRIPTION OF THE DRAWINGS

Embodiments of the invention will now be described by way of example only and with reference to the accompanying drawings, in which:—

DETAILED DESCRIPTION

Figure 1:
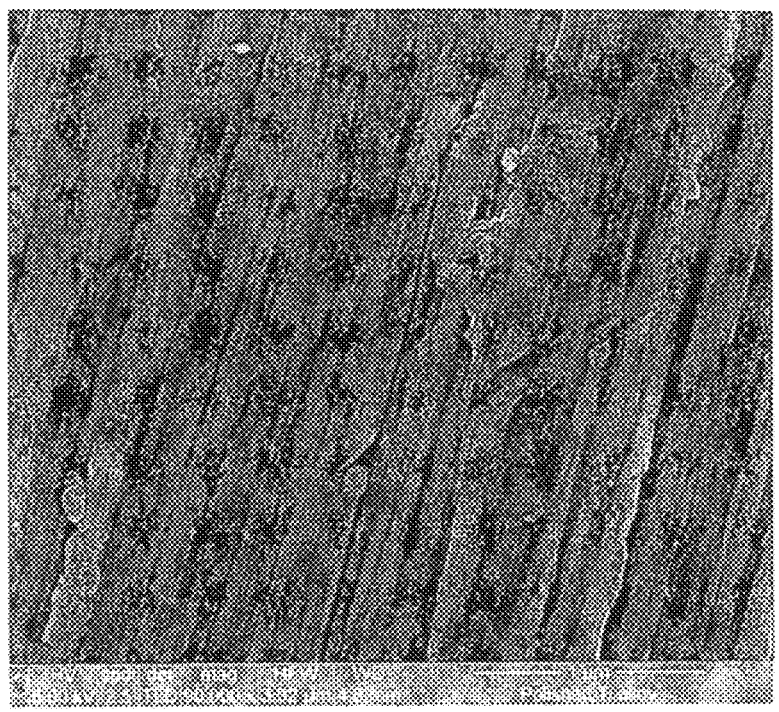
FIG. 1 is a scanning electron micrograph (SEM) of a titanium alloy surface.

Sample titanium alloy plates of various dimensions having surface areas ranging from approximately 40 mm$^2$ to 100 mm$^2$ were washed cleaned and dried to form sample substrates. The prepared or sample substrate surfaces are approximately smooth. This can be seen most clearly from FIG. 1 which is a view of the substrate surface taken by a ultra-high resolution scanning electron microscope.

A FEI Nova 200 NanoSEM ultra-high resolution Scanning Electron Microscope with a stated resolution of 1.8 nm at 3 kV and 1 nm at 15 kV using immersion optics was used to characterise primary layers formed on the titanium alloy substrate. The views or micrographs of the primary layer show detail on the nanoscale. However, it will be appreciated that other suitable methods and equipment may also be used to explore the surface detail of the primary layer.

Figure 2:
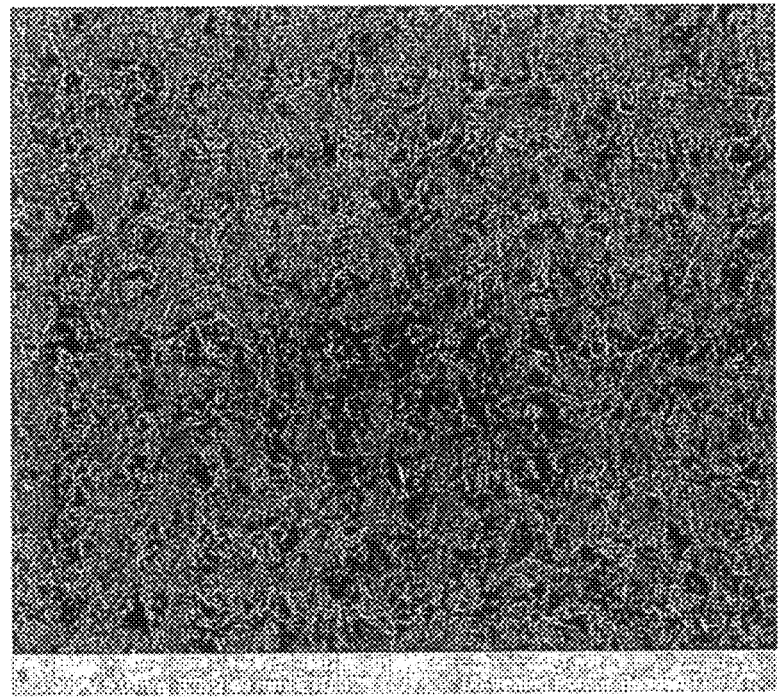
FIG. 2 is an SEM of the titanium alloy surface of FIG. 1 after grit blasting with alumina particles.
Figure 3:
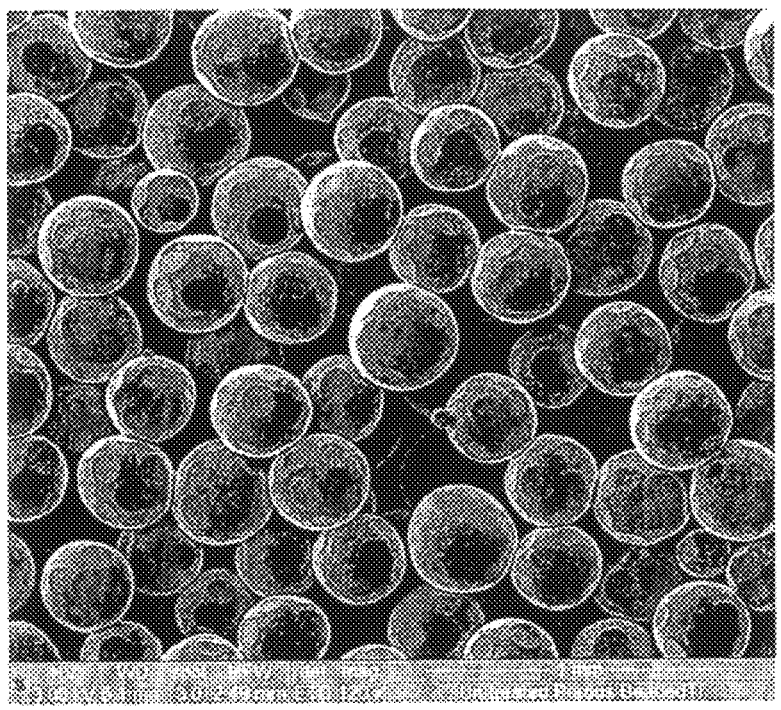
FIG. 3 is an SEM of a titanium alloy porous beaded surface.
Figure 4:
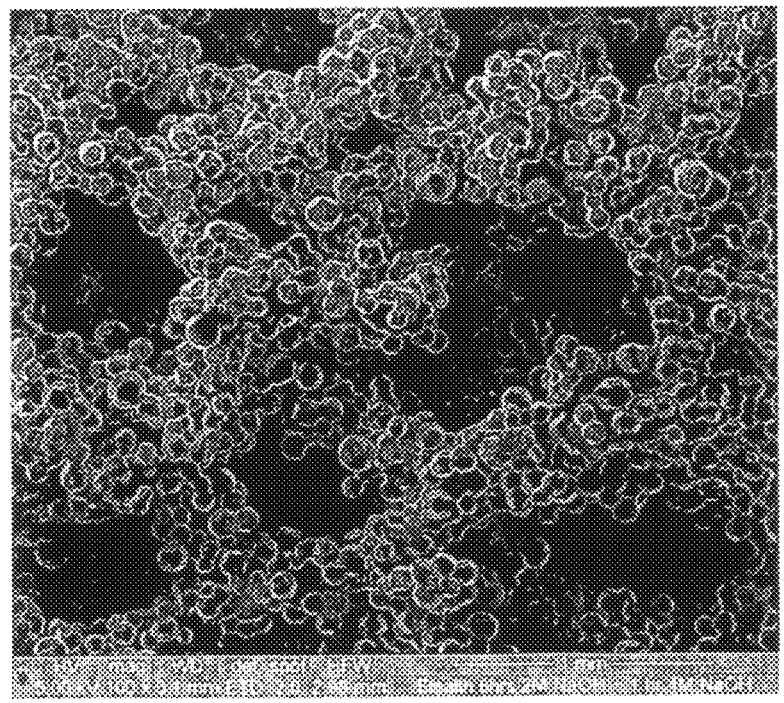
FIG. 4 is an SEM of a titanium alloy sintered bead foam surface.
Figure 5A:
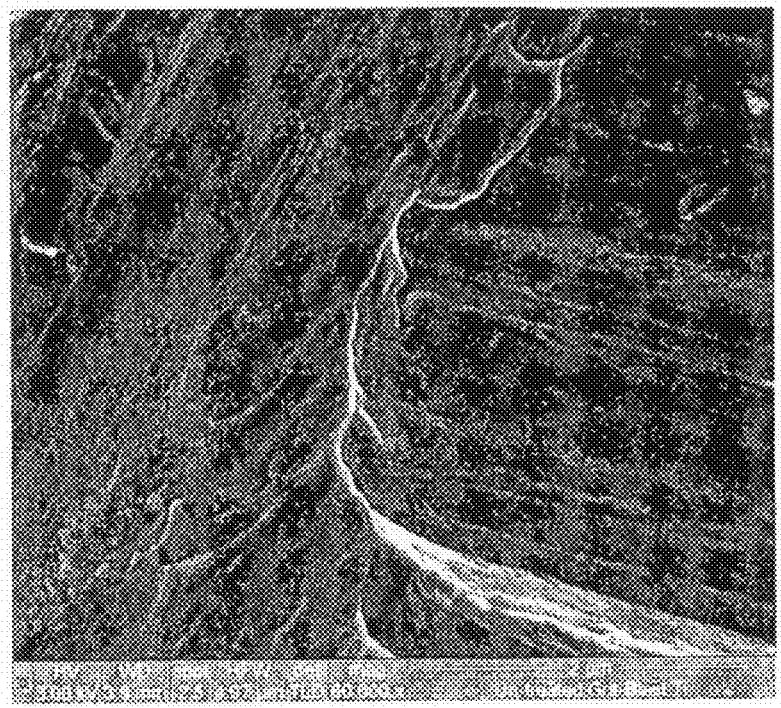
FIG. 5a is an SEM of titanium alloy surface after grit blasting with alumina particles.
Figure 5B:
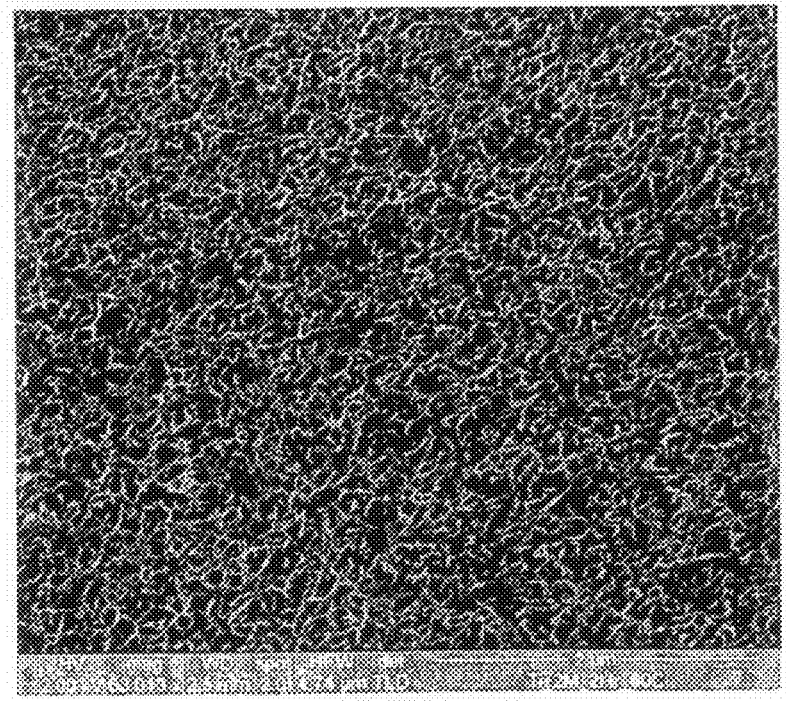
FIGS. 5b-5g are SEMs of samples of the titanium alloy surface of FIG. 5a after soaking in a 2M (2 molar), 3M, 4M, 6M, 8M and 10M solution respectively, of sodium hydroxide solution at 60° C. for 2 hours.
Figure 5C:
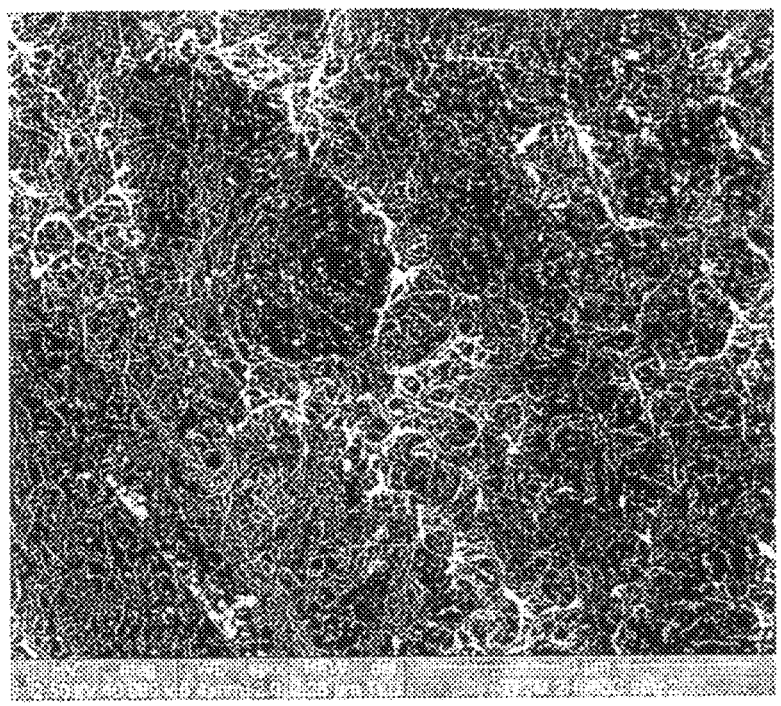
Figure 5D:
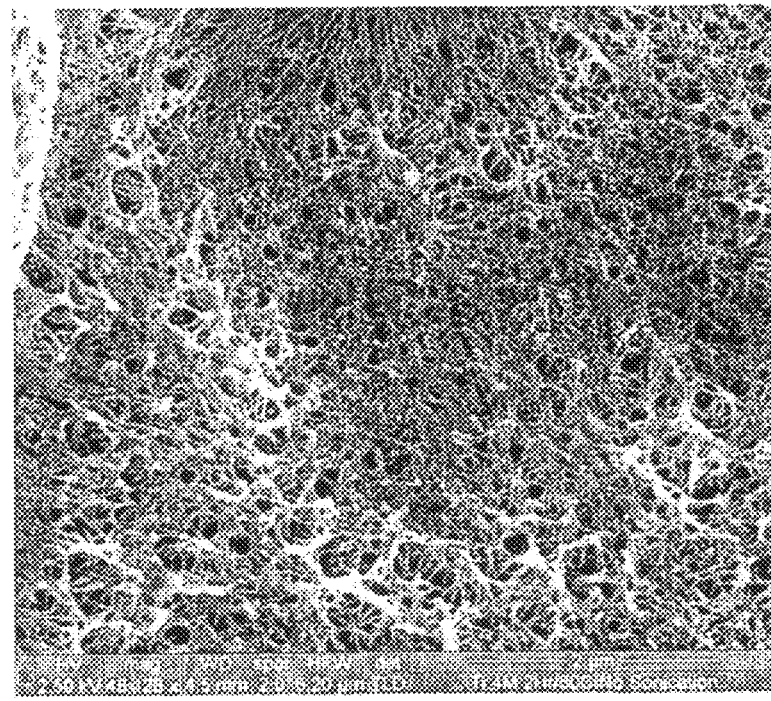
Figure 5E:
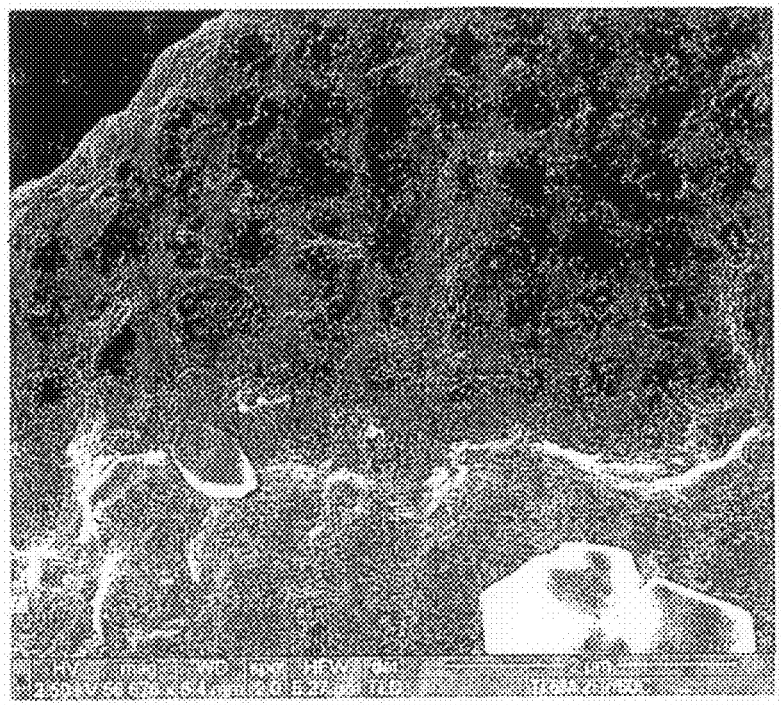
Figure 5F:
Figure 5G:
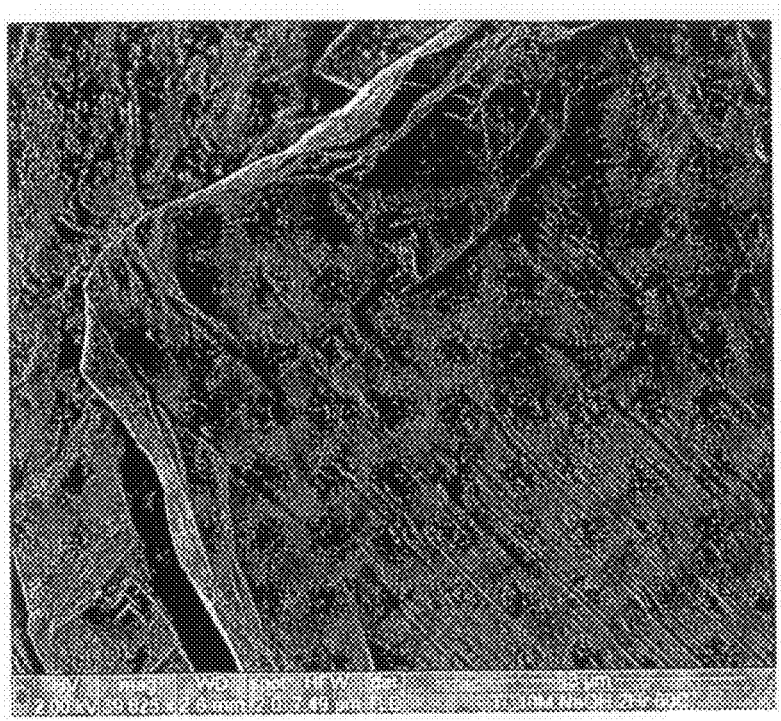

A surface of a prepared substrate sample was blasted with abrasive alumina particles otherwise known as alumina gritblast. The process of alumina grit-blasting roughens the surface of the substrate creating or partially forming a primary layer which has a greater surface area than the surface area of the prepared substrate prior to grit-blasting. This can be seen most clearly in FIGS. 2 and 5a. The primary layer was completed by soaking the substrate with the partially formed primary layer in a 4 molar solution, of sodium hydroxide at 60° C. for two hours. FIG. 5b is a view of the completed primary layer which clearly shows the development of strut-like formations, fibres or fibrils of sodium titanate having dimensions on the nanoscale. The diameter or width of these fibrils fall within the range of between 1 and 20 nanometers. Approximately 80% of the fibrils have been measured as having a diameter in the range of 5 to 12 nanometers. The length of the fibrils are between 200 and 300 nanometers.

Five further samples of the prepared substrate were alumina grit blasted and soaked in sodium hydroxide solutions of concentration 3 molar, 4 molar, 6 molar, 8 molar and 10 molar respectively at 60° C. for two hours and FIGS. 5c to 5g are views of the completed primary layer formed in each case. As can be seen from FIGS. 5c to 5g, the best etching, texturing or nanostructure formed or greatest density of fibril formation was observed where the substrate was soaked in 4 molar solution of sodium hydroxide. The greater the density of fibril formation, the greater the surface area of the primary layer. Treatment with higher concentrations of sodium hydroxide was less effective and lead to re-dissolution of the nanostructure of the primary layer resulting in a smoother surface and thus a reduced surface area.

Figure 6A:
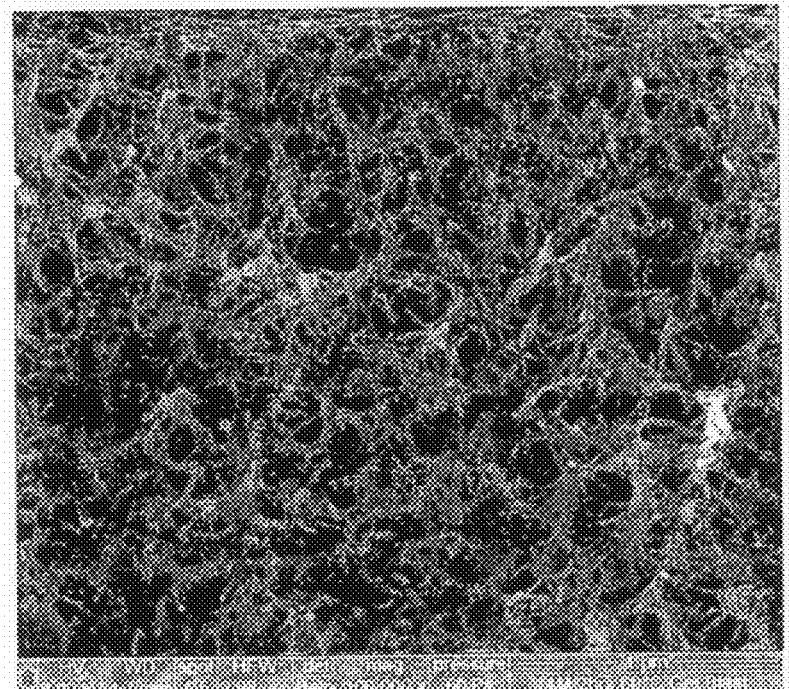
FIG. 6a-6c are SEMs of an alumina grit blast titanium alloy surface, a titanium porous beaded surface, and a titanium sintered bead foam surface respectively, soaked in a 4M sodium hydroxide solution at 60° C. for 2 hours.
Figure 6B:
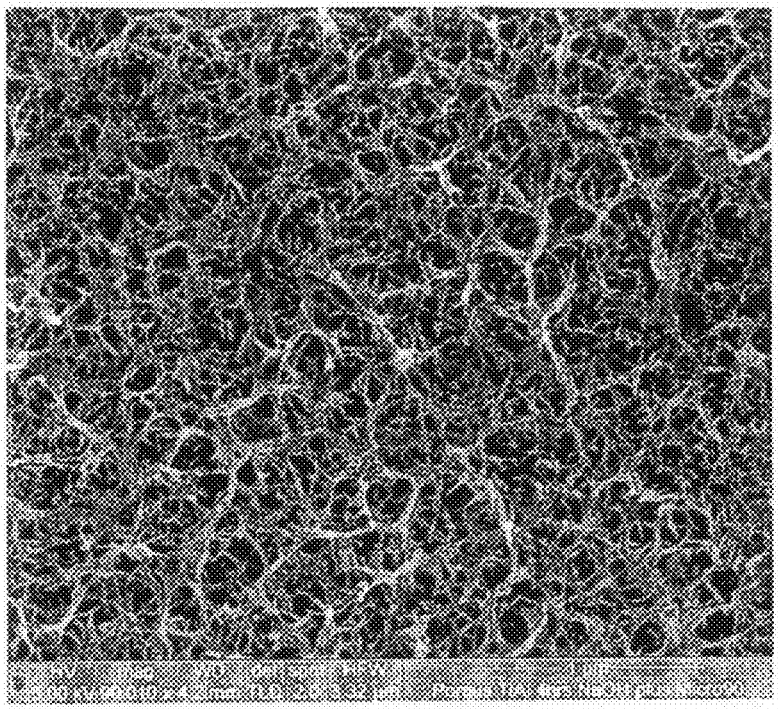
Figure 6C:
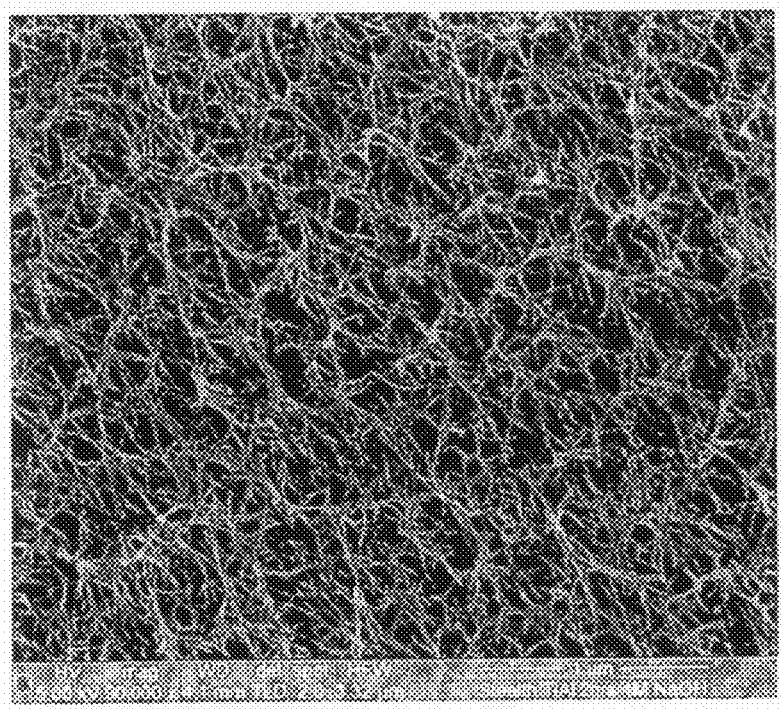
Figure 7:
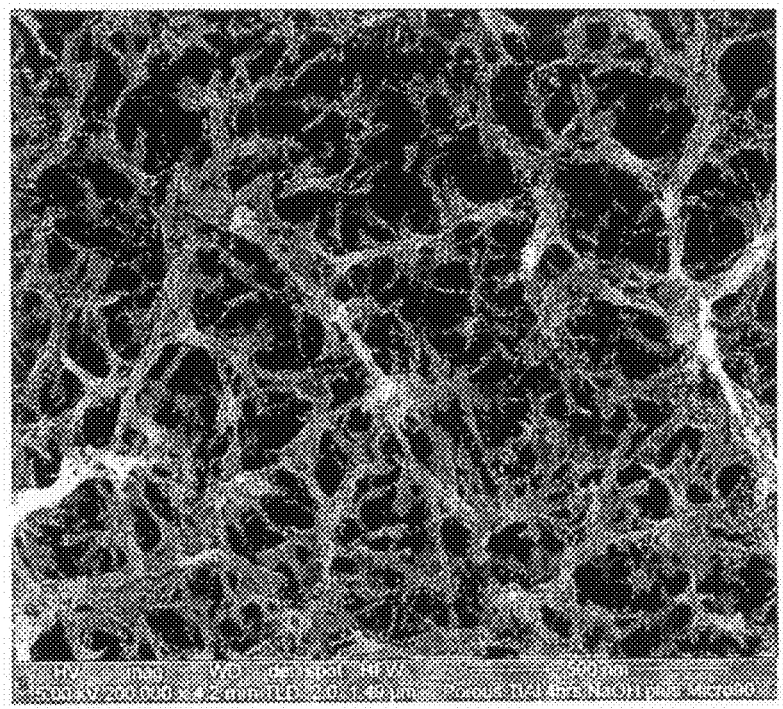
FIGS. 7 and 8 are magnified views of the titanium alloy surfaces FIG. 6b and FIG. 6c respectively.
Figure 8:
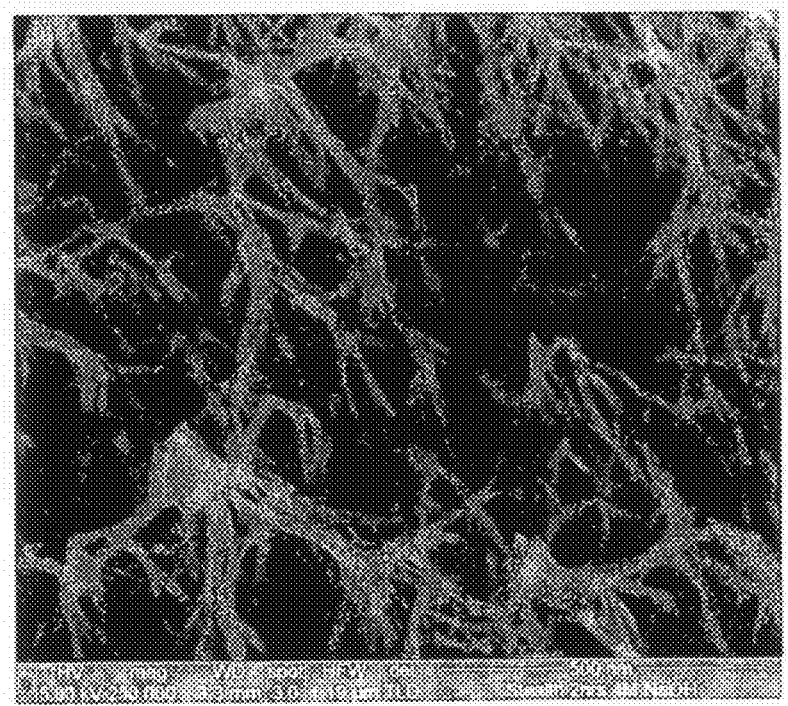

FIGS. 6a to 6c are views of a primary layer formed according to the present invention wherein the starting substrate and thus the initial topography is different in each case. FIG. 6a is a view of a primary layer which has been formed on a surface of a solid titanium alloy substrate which has been blasted with abrasive alumina particles and subsequently chemically treated by soaking in a 4 molar concentrated solution of sodium hydroxide at 60° C. for 2 hours. FIG. 6b and FIG. 6c are views of the primary layer which have been formed on a surface of a porous beaded titanium substrate and a titanium foam substrate respectively, which have been chemically treated in the same way as the solid titanium alloy substrate.

Figure 9:
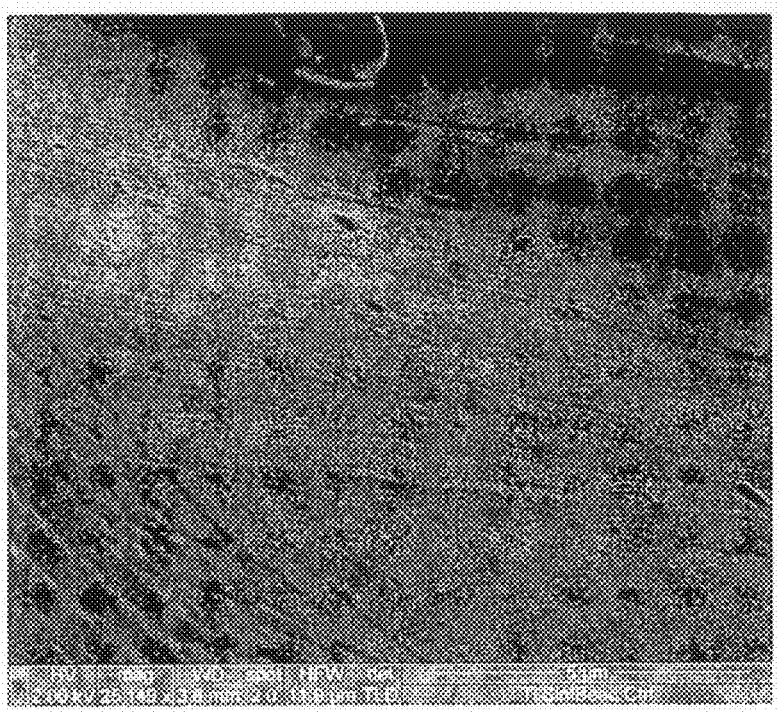
FIG. 9 is an SEM of a Porous Beaded Titanium surface prior to forming the primary layer.
Figure 10:
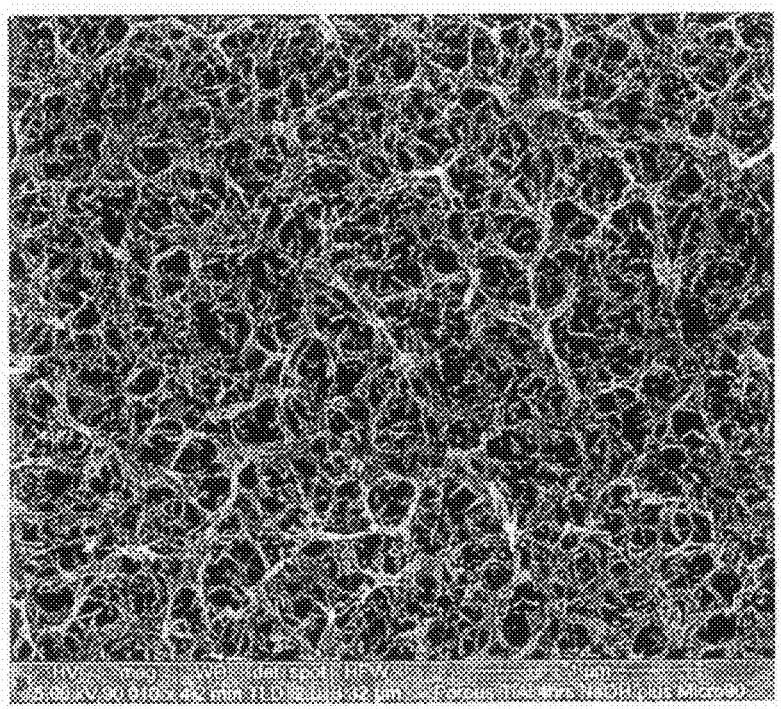
FIG. 10 is an SEM of the porous beaded titanium surface of FIG. 9, the primary layer having been formed by soaking in a 4M sodium hydroxide solution at 60° C. for 2 hours in a sonicating water bath.
Figure 11A:
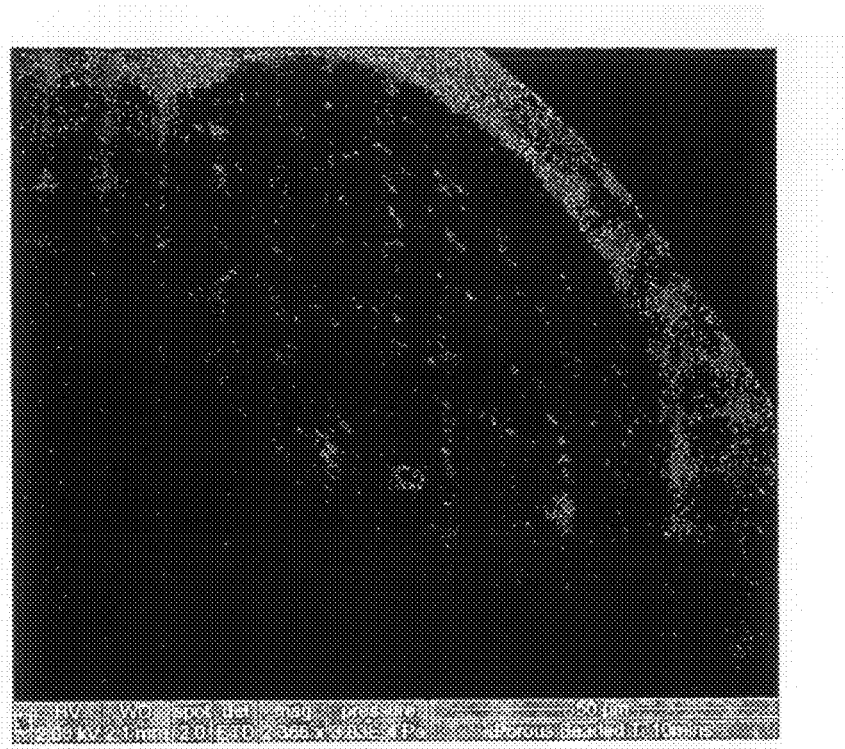
FIG. 11a is an SEM of the Porous Beaded Titanium surface of FIG. 9 soaked in a 2M solution of sodium hydroxide at 60° C. for 10 minutes.
Figure 11B:
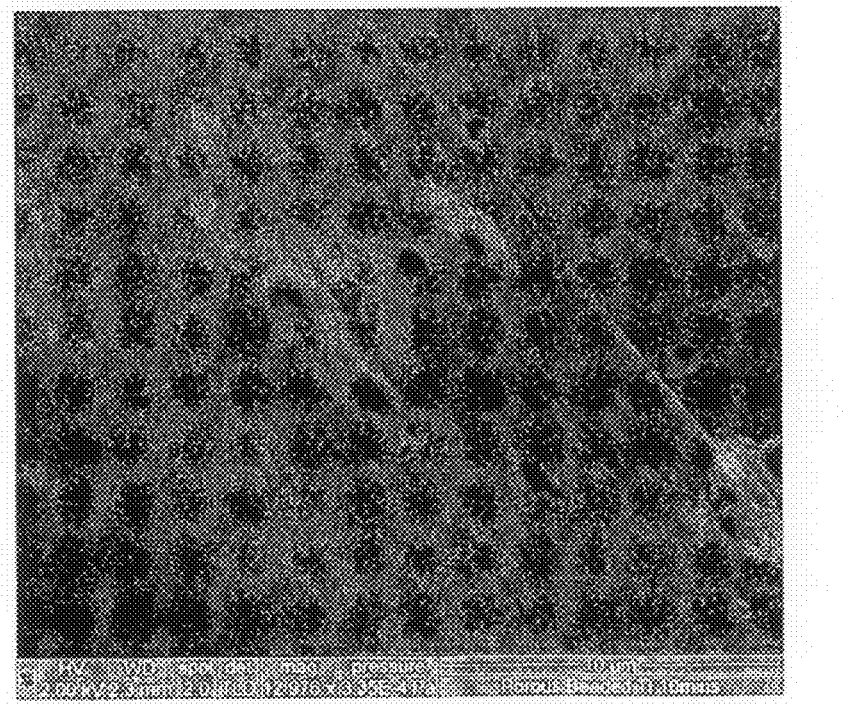
FIG. 11b is a magnified SEM of the Porous Beaded Titanium surface of FIG. 11a, more clearly showing the early formation of the nanostructured primary layer comprising nano-sized fibrils having a size in the region of 1-20 nanometers.
Figure 11C:
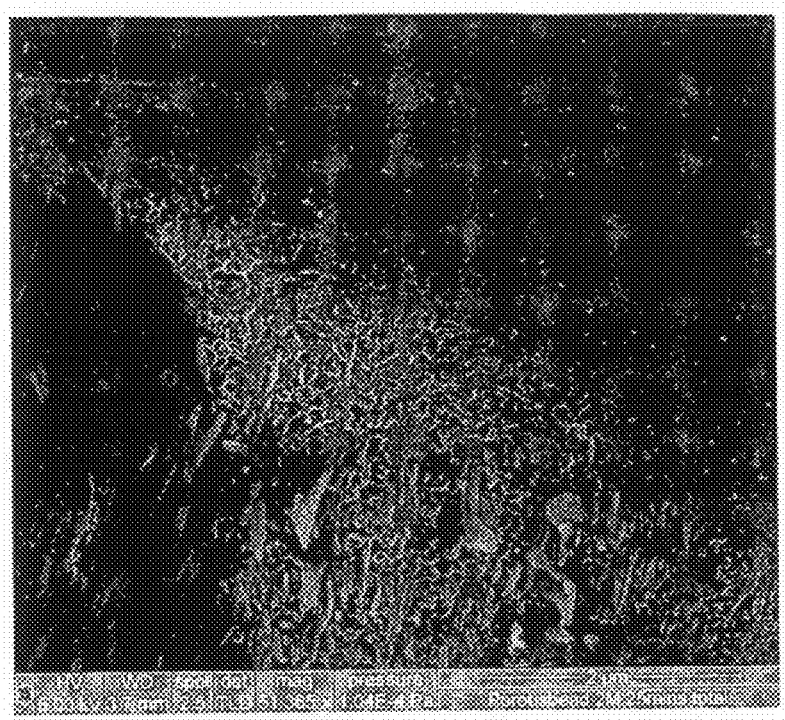
FIG. 11c is an SEM of the Porous Beaded Titanium surface of FIG. 11a soaked in a 2 Molar solution of sodium hydroxide at 60° C. for a further 15 minutes clearly showing the development of the nanostructured primary layer.
Figure 11D:
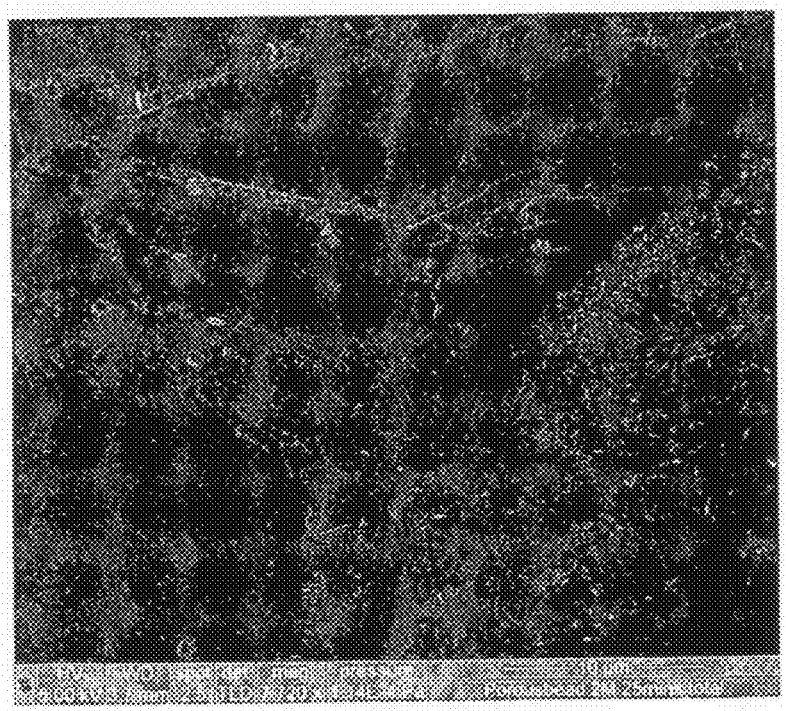
FIG. 11d is an SEM of a different portion of the Porous Beaded Titanium surface of FIG. 11a clearly showing the irregular nature of the formation of the primary layer.
Figure 12:
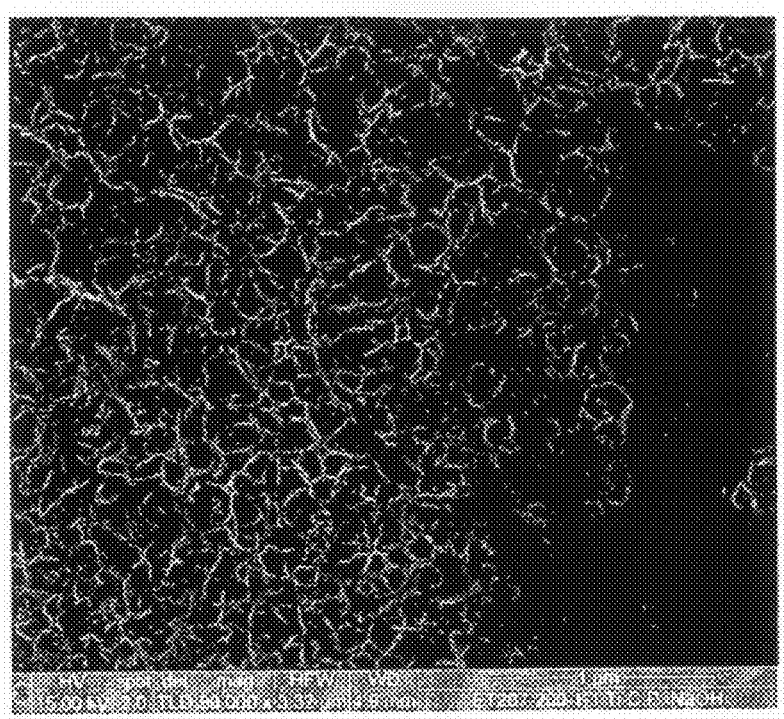
FIG. 12 is an SEM of a commercially pure titanium surface after grit blasting with alumina particles with subsequent soaking in a 4M solution of sodium hydroxide solution at 60° C. for 2 hours.

The porous beaded titanium substrate and titanium foam substrate were not subjected to any physical treatment such as in the case of the solid titanium alloy substrate. It was found that the greater the surface area of the starting substrate, the greater the surface area of the primary layer formed. As can be quite clearly seen from FIGS. 6a to 6c the fibrils formed in the case of the titanium foam substrate, which had the greatest starting substrate surface area, were the most fine, and thus fibril formation density was greatest presenting the highest primary layer surface area. FIG. 9 is an SEM of a portion of a surface of a porous beaded titanium alloy prior to completing the primary layer. FIGS. 11a to 11d illustrate the development of the primary layer over time when soaked in a 2 molar solution of sodium hydroxide at 60° C.

Figure 13A:
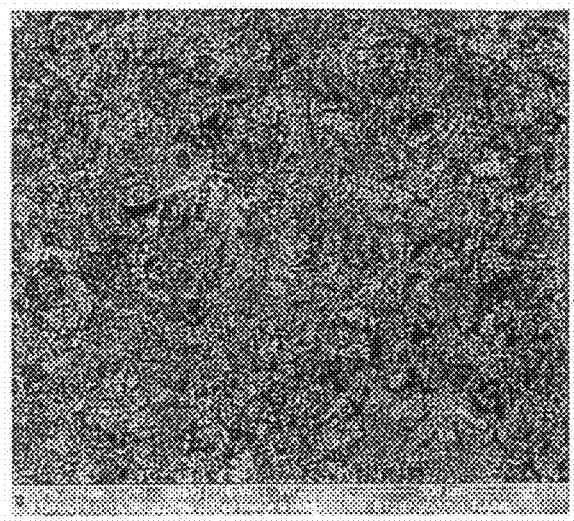
FIGS. 13a-13c are SEMs of increasing magnification of areas of the surface of TiAlNb alloy after grit blasting with alumina particles but prior to soaking in sodium hydroxide, the SEM employing a 2 kv beam to analyse the upper structure of the primary layer created.
Figure 13B:
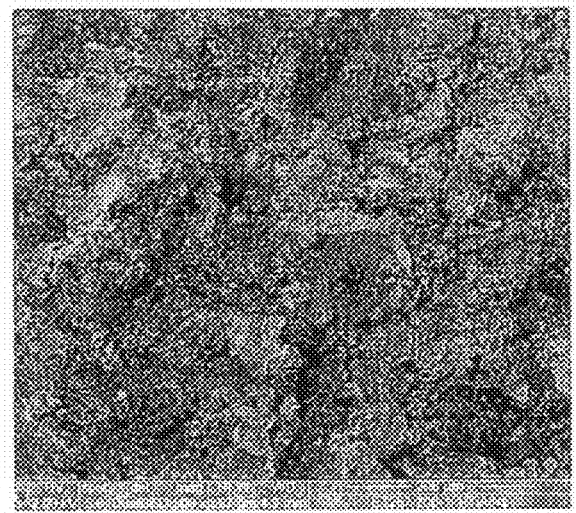
Figure 13C:
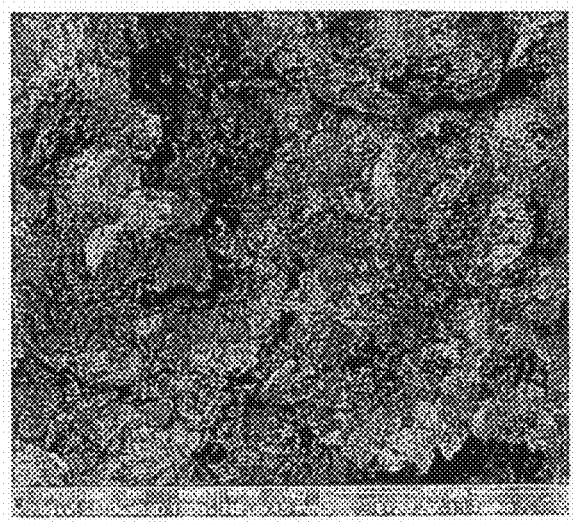
Figure 14A:
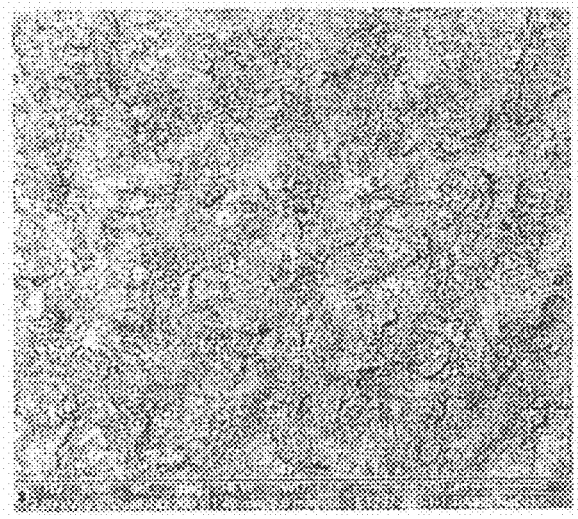
FIGS. 14a-14c are SEMs of the same areas of the surface of the TiAlNb alloy of FIGS. 13a-13c after soaking in 4M sodium hydroxide solution at 60° C. for 2 hours, the SEM employing a 2 kv beam to analyse the upper structure of the completed primary layer.
Figure 14B:
Figure 14C:
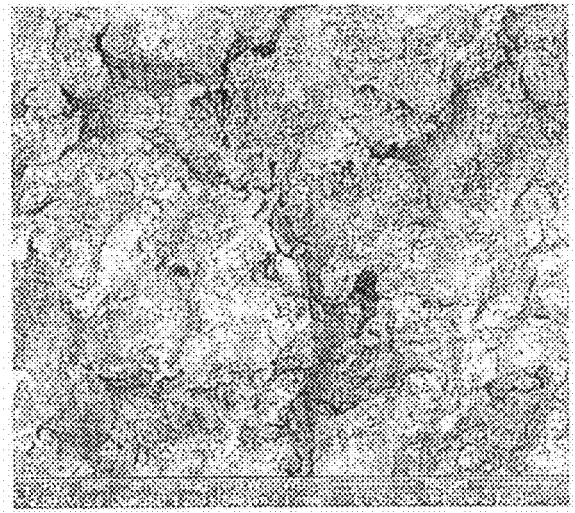
Figure 15A:
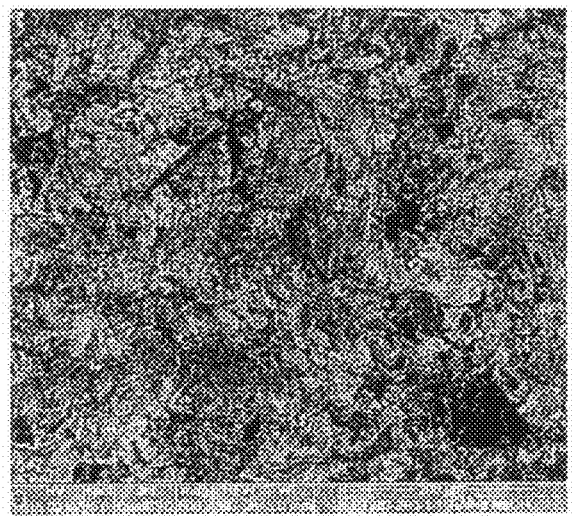
FIGS. 15a and 15b are SEMs of the same areas of the surface of the TiAlNb alloy of FIGS. 14b and 14c respectively, the SEM employing a 15 kv beam to analyse the substructure of the completed primary layer.
Figure 15B:
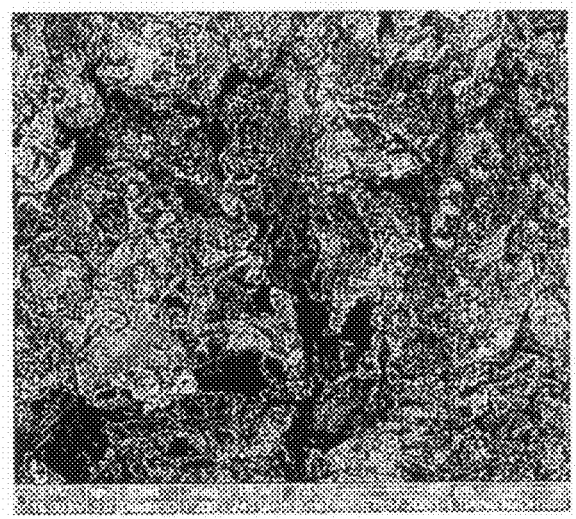
Figure 16:
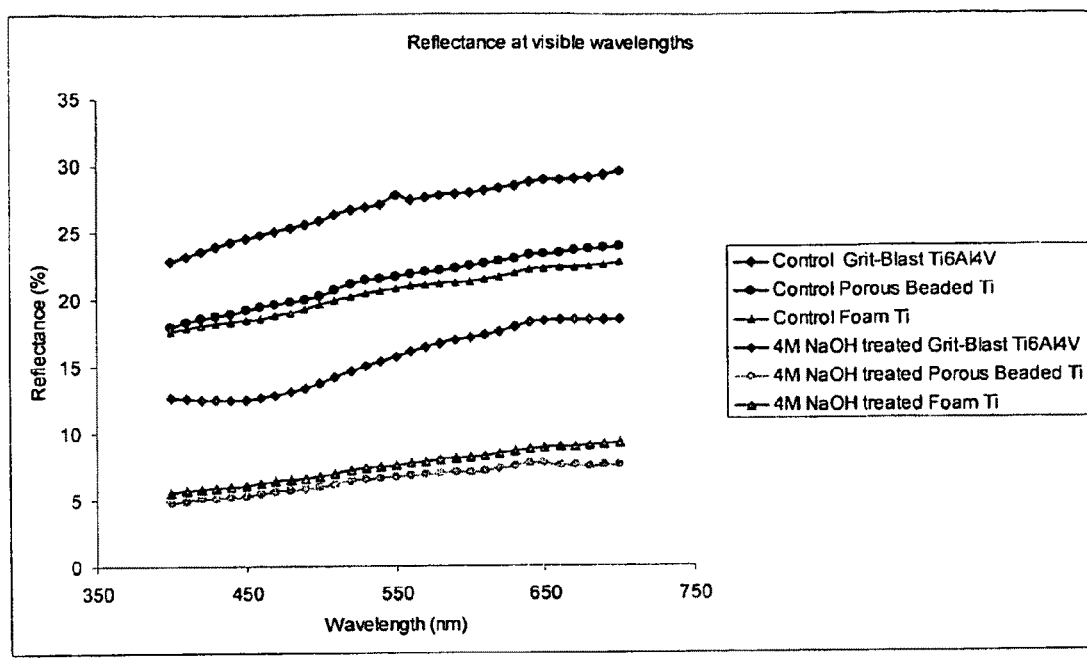
FIG. 16 is a graph showing the percentage reflectance from the surface of the primary layer for different substrates.
Figure 17A:
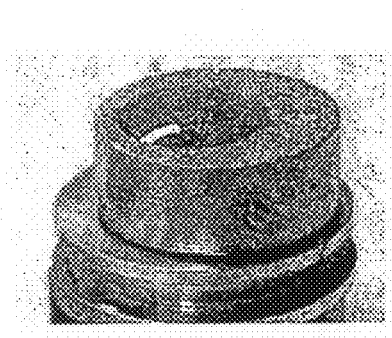
FIGS. 17a and 17b are pictorial views of samples of the material according to the present invention showing the primary layer prior to treatment with sodium hydroxide and post treatment with sodium hydroxide respectively.
Figure 17B:
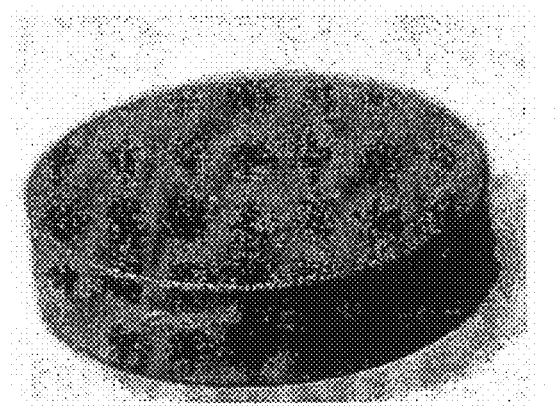
Figure 18:
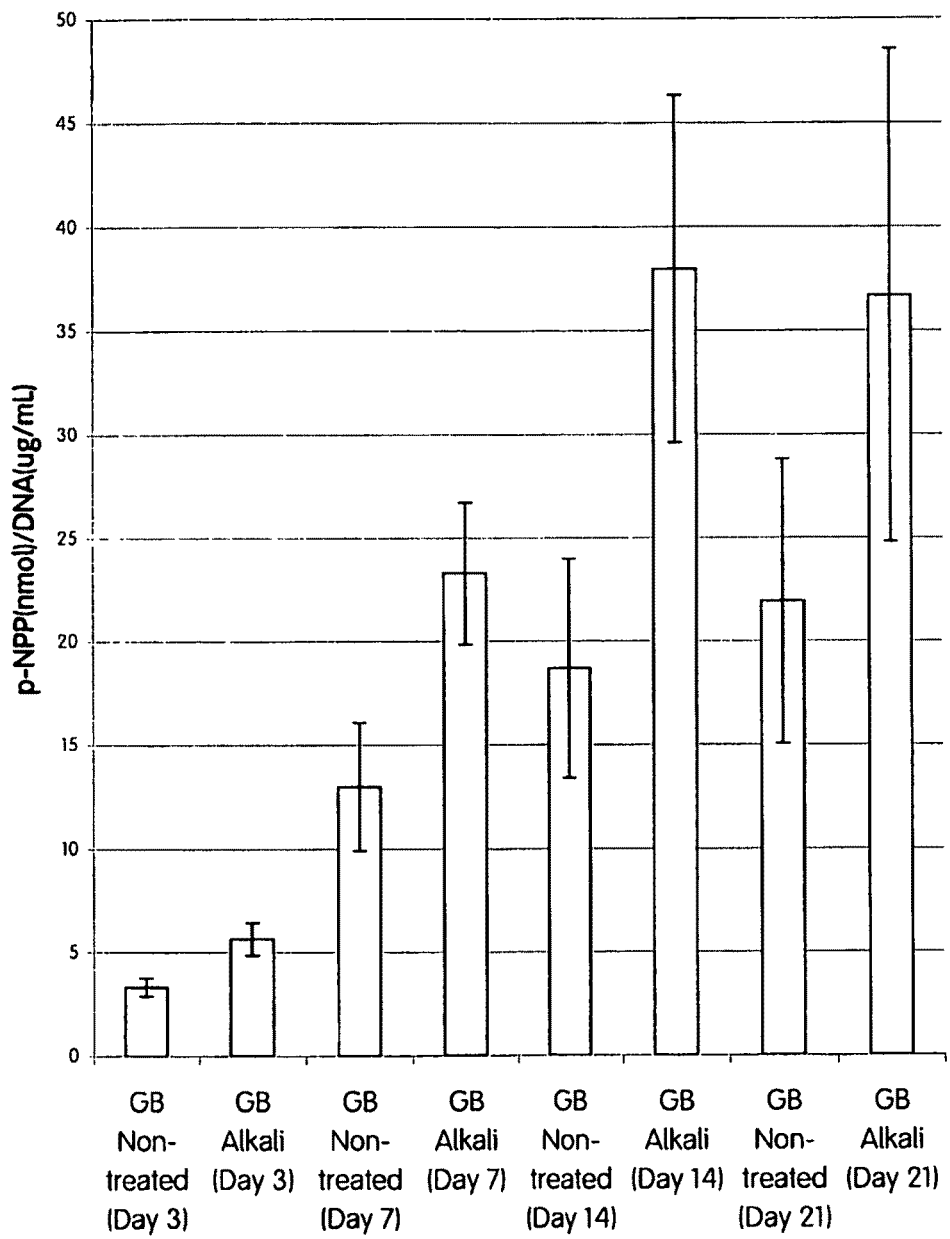
FIG. 18 shows grit blasted titanium coupons p-NPP data normalised to DNA (Pico Green) with error bars of standard deviation. This data is from Table 2.
Figure 19:
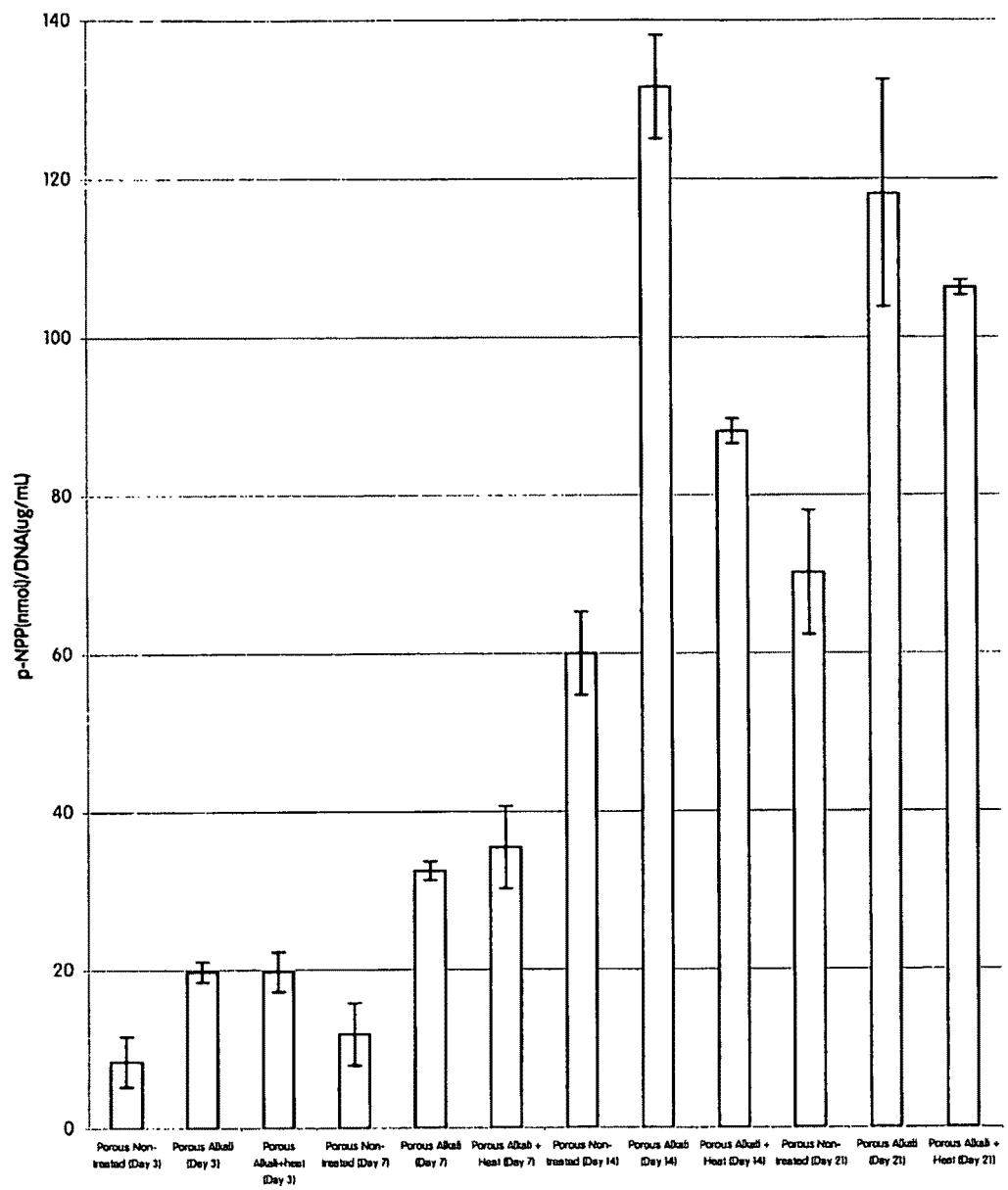
FIG. 19 shows porous beaded titanium coupons p-NPP data normalised to DNA (Pico Green) with error bars of standard deviation. This data is from Table 3.
Figure 20:
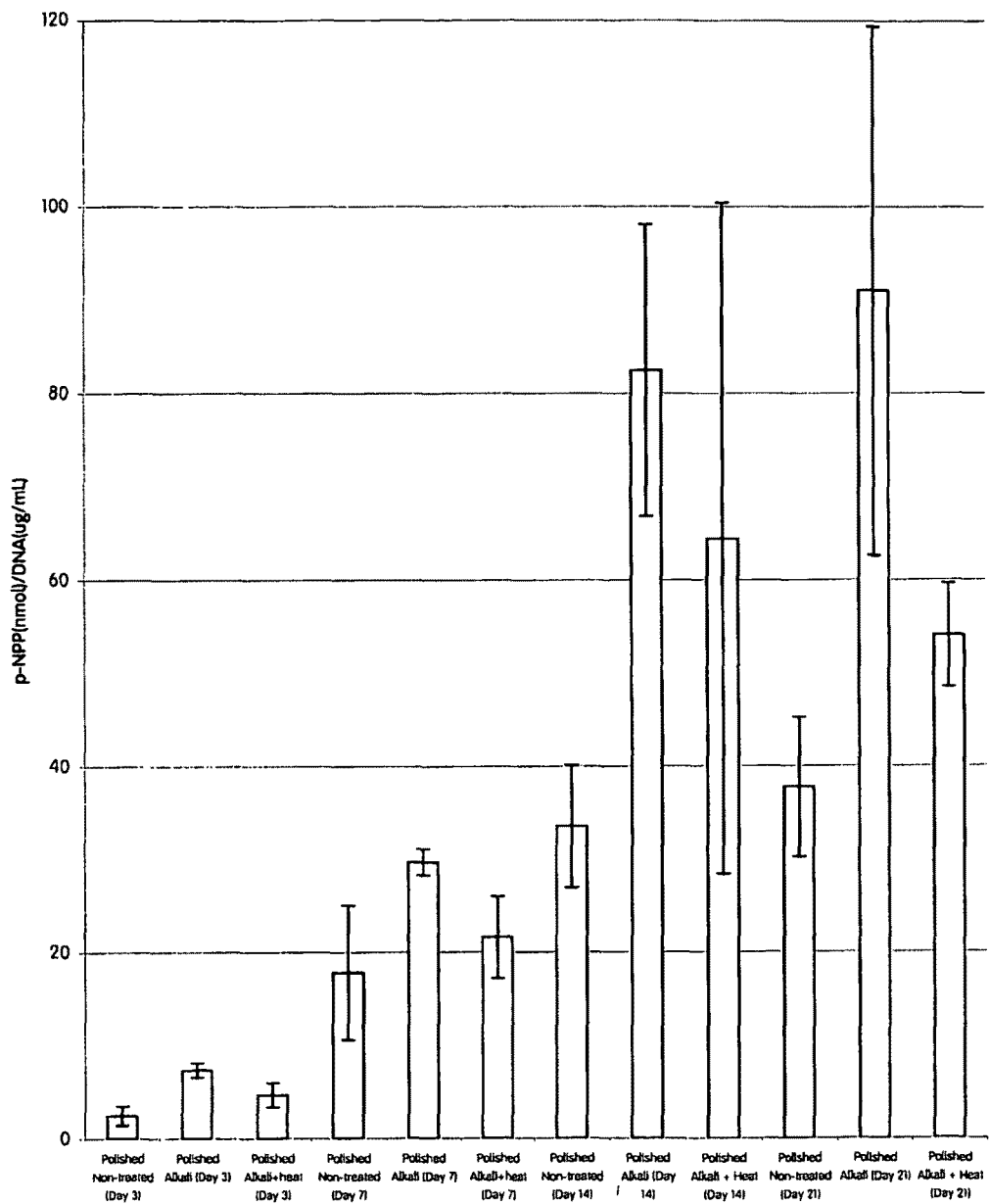
FIG. 20 shows polished titanium coupons p-NPP data normalised to DNA (Pico Green) with error bars of standard deviation. This data is from Table 4.

FIGS. 13a-13c are SEMs of increasing magnification (200, 500 and 1200 times magnified respectively) of areas of the surface of TiAlNb alloy after grit blasting with alumina particles but prior to soaking in sodium hydroxide; the SEM employing a 2 kv beam to analyse the upper structure of the completed primary layer. FIGS. 14a-14c are SEMs of the same areas and at the same magnifications of the surface of the TiAlNb alloy of FIGS. 13a-13c respectively after soaking in 4 molar sodium hydroxide solution at 60° C. for 2 hours; the SEM employing a 2 kv beam to analyse the upper structure of the primary layer thus formed. FIGS. 15a and 15b are SEMs of same areas and at the same magnifications, of the surface of the TiAlNb alloy of FIGS. 13b and 13c respectively; the SEM employing a 15 kv beam to analyse the substructure of the primary layer formed.

The surfaces of the primary layers were analysed by scanning electron microscopy (SEM) before and after soaking the substrate in sodium hydroxide solution to analyse surface topography and alumina content throughout the primary layer. This technique can be carried out at different voltages which enables the surface and subsurface of the primary layer to be analysed; the greater the voltage the deeper the penetration of the beam. Titanium alloy has a higher average atomic number than alumina. The higher the average atomic number of the material being analysed using SEM, the greater will be the electron backscatter and thus the brighter will be the SEM image.

Alumina has an average atomic number less than titanium alloy and thus an SEM image of titanium alloy with alumina present is darker than titanium alloy without alumina. It is quite clear when comparing FIG. 1, which shows a titanium alloy substrate prior to alumina grit blasting, with FIGS. 13a to 13c, for example, which show the titanium alloy substrate post alumina grit blasting, that quite a substantial amount of alumina becomes embedded in the surface of the substrate forming the primary layer. FIGS. 14a to 14c represent the primary layer of FIGS. 13a to 13c which have been completed by chemical treatment with sodium hydroxide as described above. As can be seen, the SEM images of the primary layer illustrated in FIGS. 14a to 14c are brighter than the SEM images of the primary layer illustrated in FIGS. 13a to 13c because the sodium titanate layer formed masks the alumina particles present in the upper surface of the primary layer. Sodium titanate has an average atomic number higher than that of alumina and thus the SEM image of the completed primary layer will appear brighter than the primary layer created by alumina grit blasting and prior to treatment with sodium hydroxide.

The higher voltage SEM images illustrate the composition of the subsurface of the primary layer which is clearly darker and thus higher in alumina content than the upper surface regions. However, it is only critical to mask the alumina particles in the upper surface of the primary layer which forms the implant-to-bone interface and thus is in direct contact with the bone, as contamination of the subsurface of the primary layer with abrasive particles has little affect on the bond formed between the bone and implant.

Analysis of the reflectance of various substrates prior to and after treatment with 4 molar sodium hydroxide was also undertaken. As can be seen quite clearly from table 1 below, the greater the surface area of the primary layer, the less visible light is reflected. The titanium foam substrate which produced the primary layer having the greatest surface area reflected only between 5 and 10% of the visible light. All the primary layers completed were black in colour when viewed by the naked eye.

TABLE 1

| Wavelength (nm) | Control Grit-Blast Ti6Al4V | Control Porous Beaded Ti | Control Foam Ti | 4M NaOH treated Grit-Blast Ti6Al4V | 4M NaOH treated Porous Beaded Ti | 4M NaOH treated Foam Ti |
| --- | --- | --- | --- | --- | --- | --- |
| 400 | 22.83 | 17.99 | 17.61 | 12.71 | 4.78 | 5.56 |
| 410 | 23.23 | 18.32 | 17.86 | 12.61 | 4.94 | 5.71 |
| 420 | 23.6 | 18.58 | 18.05 | 12.53 | 5.06 | 5.82 |
| 430 | 23.95 | 18.75 | 18.19 | 12.47 | 5.12 | 5.88 |
| 440 | 24.26 | 18.92 | 18.3 | 12.47 | 5.18 | 5.96 |
| 450 | 24.55 | 19.17 | 18.44 | 12.54 | 5.31 | 6.1 |
| 460 | 24.82 | 19.42 | 18.6 | 12.67 | 5.45 | 6.25 |
| 470 | 25.11 | 19.6 | 18.8 | 12.88 | 5.59 | 6.39 |
| 480 | 25.39 | 19.79 | 19.03 | 13.14 | 5.72 | 6.53 |
| 490 | 25.64 | 19.99 | 19.31 | 13.41 | 5.84 | 6.63 |
| 500 | 25.92 | 20.28 | 19.61 | 13.74 | 5.98 | 6.76 |
| 510 | 26.3 | 20.75 | 19.92 | 14.18 | 6.2 | 7 |
| 520 | 26.67 | 21.19 | 20.21 | 14.63 | 6.4 | 7.23 |
| 530 | 26.89 | 21.4 | 20.42 | 14.99 | 6.51 | 7.37 |
| 540 | 27.07 | 21.54 | 20.61 | 15.33 | 6.6 | 7.49 |

TABLE 1-continued

| Wavelength (nm) | Control Grit-Blast Ti6Al4V | Control Porous Beaded Ti | Control Foam Ti | 4M NaOH treated Grit-Blast Ti6Al4V | 4M NaOH treated Porous Beaded Ti | 4M NaOH treated Foam Ti |
|---|---|---|---|---|---|---|
| 550 | 27.76 | 21.72 | 20.8 | 15.7 | 6.7 | 7.61 |
| 560 | 27.44 | 21.89 | 20.97 | 16.06 | 6.8 | 7.74 |
| 570 | 27.6 | 22.02 | 21.09 | 16.41 | 6.91 | 7.88 |
| 580 | 27.74 | 22.15 | 21.19 | 16.72 | 7 | 8.01 |
| 590 | 27.87 | 22.32 | 21.27 | 16.95 | 7.02 | 8.1 |
| 600 | 27.99 | 22.51 | 21.35 | 17.15 | 7.04 | 8.19 |
| 610 | 28.12 | 22.68 | 21.48 | 17.36 | 7.15 | 8.31 |
| 620 | 28.28 | 22.85 | 21.67 | 17.6 | 7.3 | 8.46 |
| 630 | 28.52 | 23.06 | 21.95 | 17.95 | 7.54 | 8.63 |
| 640 | 28.78 | 23.27 | 22.23 | 18.29 | 7.74 | 8.8 |
| 650 | 28.9 | 23.4 | 22.34 | 18.42 | 7.73 | 8.92 |
| 660 | 28.96 | 23.51 | 22.38 | 18.45 | 7.62 | 9 |
| 670 | 29.04 | 23.65 | 22.41 | 18.46 | 7.55 | 9.06 |
| 680 | 29.14 | 23.79 | 22.46 | 18.47 | 7.52 | 9.11 |
| 690 | 29.31 | 23.88 | 22.59 | 18.48 | 7.55 | 9.18 |
| 700 | 29.52 | 23.94 | 22.78 | 18.49 | 7.63 | 9.27 |

Sample titanium materials, titanium alloy coupons, having different pre-treatments (grit blasted, polished, porous beaded) were compared for osteogenic activity on the surface after being chemically treated with an alkaline solution, compared to each other type and of pre-treatment and to not being chemically treated.

The alkaline solution was a 4 molar solution of sodium hydroxide for 2 hours at 60° (as described here before).

The pre-treatments of the titanium alloy coupons were polishing the surface, grit blasting and porous beading as known in the art.

After the chemical treatment the titanium alloy coupons were inserted into individual silicone tubes so that any fluid placed on to the coupon remained on the test surface. Coupons were then sterilised.

Human mesenchymal stem cells were resurrected and passaged in suitable medium and incubated overnight. After incubation the medium was replaced with an osteogenic medium containing β-Glycerophosphate and this was changed twice a week.

Live/dead staining on the cells was performed on all surface types at all time points.

The samples were subject to cell lysis and P-nitrophenol alkaline phosphatase p-NPP assay analysis to indicated osteogenic activity of the cells and thus, bone formation.

The results are as shown in Table 2 for grit blasted pre-treated coupons alkaline solution treated compared to not being subject to alkaline solution.

TABLE 2

| | Grit blasted | GB Non-treated (Day 3) | GB Alkali (Day 3) | GB Non-treated (Day 7) | GB Alkali (Day 7) | GB Non-treated (Day 14) | GB Alkali (Day 14) | GB Non-treated (Day 21) | GB Alkali (Day 21) |
|---|---|---|---|---|---|---|---|---|---|
| p-NPP | Rep 1 | 25.493 | 38.760 | 79.569 | 155.813 | 165.721 | 211.735 | 149.917 | 226.772 |
| | Rep 2 | 21.630 | 37.081 | 63.447 | 142.378 | 184.362 | 263.529 | 228.443 | 380.482 |
| | Rep 3 | 19.783 | 36.745 | 95.859 | 129.446 | 235.583 | 306.969 | 243.480 | 327.018 |
| Pico Green | Rep 1 | 6.702 | 5.965 | 5.227 | 7.439 | 11.863 | 7.439 | 10.388 | 9.651 |
| | Rep 2 | 6.702 | 6.702 | 6.702 | 5.227 | 10.388 | 5.965 | 8.176 | 8.176 |
| | Rep 3 | 6.702 | 7.439 | 6.702 | 5.965 | 9.651 | 7.439 | 10.388 | 8.176 |
| Normalisation | Rep 1 | 3.804 | 6.498 | 15.222 | 20.945 | 13.970 | 28.463 | 14.432 | 23.498 |
| | Rep 2 | 3.228 | 5.533 | 9.467 | 27.237 | 17.748 | 44.183 | 27.940 | 46.535 |
| | Rep 3 | 2.952 | 4.939 | 14.304 | 21.703 | 24.411 | 41.265 | 23.439 | 39.996 |
| | Mean | 3.328 | 5.657 | 12.998 | 23.295 | 18.709 | 37.970 | 21.937 | 36.676 |
| | Standard deviation | 0.435 | 0.787 | 3.092 | 3.435 | 5.286 | 8.362 | 6.878 | 11.872 |

Table 3 shows pre-treated porous beaded coupons with and without alkaline solution treatment.

TABLE 3

| | Porous beaded | Porous Non-treated (Day 3) | Porous Alkali (Day 3) | Porous Alkali + heat (Day 3) | Porous Non-treated (Day 7) | Porous Alkali (Day 7) | Porous Alkali + Heat (Day 7) | Porous Non-treated (Day 14) | Porous Alkali (Day 14) | Porous Alkali + Heat (Day 14) | Porous Non-treated (Day 21) | Porous Alkali (Day 21) | Porous Alkali + Heat (Day 21) |
|---|---|---|---|---|---|---|---|---|---|---|---|---|---|
| p-NPP | Rep 1 | 74.363 | 125.584 | 150.271 | 76.404 | 295.273 | 198.369 | 612.718 | 1137.336 | 734.683 | 636.108 | 744.708 | 945.199 |
| | Rep 2 | 75.874 | 161.187 | 187.553 | 153.259 | 322.005 | 250.163 | 617.730 | 1132.324 | 709.622 | 843.282 | 968.589 | 1035.420 |
| | Rep 3 | 94.851 | 151.278 | 174.622 | 139.893 | 231.784 | 265.200 | 729.671 | 1052.127 | 846.624 | 764.757 | 1100.579 | 1017.041 |

TABLE 3-continued

| | | Porous beaded | Porous Non-treated (Day 3) | Porous Alkali (Day 3) | Porous Alkali + heat (Day 3) | Porous Non-treated (Day 7) | Porous Alkali (Day 7) | Porous Alkali + Heat (Day 7) | Porous Non-treated (Day 14) | Porous Alkali (Day 14) | Porous Alkali + Heat (Day 14) | Porous Non-treated (Day 21) | Porous Alkali (Day 21) | Porous Alkali + Heat (Day 21) |
|---|---|---|---|---|---|---|---|---|---|---|---|---|---|---|
| Pico Green | Rep 1 | 14.074 | 5.965 | 8.914 | 10.388 | 8.914 | 6.702 | 11.125 | 8.176 | 8.176 | 10.388 | 6.702 | 8.914 |
| | Rep 2 | 8.914 | 8.176 | 8.914 | 11.125 | 9.651 | 6.702 | 10.388 | 8.914 | 8.176 | 11.125 | 8.914 | 9.651 |
| | Rep 3 | 8.176 | 8.176 | 8.176 | 9.651 | 7.439 | 6.702 | 11.125 | 8.176 | 9.651 | 10.388 | 8.176 | 9.651 |
| Normalisation | Rep 1 | 5.284 | 21.055 | 16.859 | 7.355 | 33.126 | 29.600 | 55.074 | 139.102 | 89.855 | 61.235 | 111.121 | 106.041 |
| | Rep 2 | 8.512 | 19.714 | 21.041 | 13.776 | 33.366 | 37.328 | 59.466 | 127.034 | 86.790 | 75.799 | 108.665 | 107.289 |
| | Rep 3 | 11.601 | 18.502 | 21.357 | 14.495 | 31.158 | 39.572 | 65.587 | 128.681 | 87.726 | 73.619 | 134.606 | 105.384 |
| | Mean | 8.466 | 19.757 | 19.752 | 11.875 | 32.550 | 35.500 | 60.042 | 131.606 | 88.124 | 70.218 | 118.131 | 106.238 |
| | Standard deviation | 3.159 | 1.277 | 2.511 | 3.931 | 1.212 | 5.231 | 5.280 | 6.544 | 1.571 | 7.855 | 14.321 | 0.967 |

Table 4 shows polished coupons with and without alkaline solution treatment.

TABLE 4

| | | Polished | Polished Non-treated (Day 3) | Polished Alkali (Day 3) | Polished Alkali + heat (Day 3) | Polished Non-treated (Day 7) | Polished Alkali (Day 7) | Polished Alkali + heat (Day 7) |
|---|---|---|---|---|---|---|---|---|
| p-NPP | Rep 1 | | 20.287 | 37.920 | 38.088 | 136.668 | 186.209 | 87.630 |
| | Rep 2 | | 24.149 | 34.729 | 31.203 | 94.683 | 152.958 | 118.866 |
| | Rep 3 | | 20.119 | 36.913 | 31.203 | 67.477 | 148.927 | 132.133 |
| Pico Green | Rep 1 | | 8.914 | 5.227 | 6.702 | 5.965 | 5.965 | 5.227 |
| | Rep 2 | | 6.702 | 5.227 | 9.651 | 7.439 | 5.227 | 5.227 |
| | Rep 3 | | 12.600 | 4.490 | 5.965 | 22.921 | 5.227 | 5.227 |
| Normalisation | Rep 1 | | 2.276 | 7.254 | 5.683 | 22.913 | 31.220 | 16.764 |
| | Rep 2 | | 3.603 | 6.644 | 3.233 | 12.728 | 29.261 | 22.740 |
| | Rep 3 | | 1.597 | 8.221 | 5.231 | 2.944 | 28.490 | 25.278 |
| | Mean | | 2.492 | 7.373 | 4.716 | 17.821 | 29.657 | 21.594 |
| | Standard deviation | | 1.021 | 0.795 | 1.304 | 7.202 | 1.407 | 4.371 |

| | | Polished | Polished Non-treated (Day 14) | Polished Alkali (Day 14) | Polished Alkali + Heat (Day 14) | Polished Non-treated (Day 21) | Polished Alkali (Day 21) | Polished Alkali + Heat (Day 21) |
|---|---|---|---|---|---|---|---|---|
| p-NPP | Rep 1 | | 206.723 | 527.509 | 158.271 | 288.590 | −15.488 | −20.500 |
| | Rep 2 | | 265.200 | 470.703 | 357.091 | 352.079 | 908.442 | 484.069 |
| | Rep 3 | | 196.699 | 554.241 | 731.342 | 7.903 | 527.509 | 388.836 |
| Pico Green | Rep 1 | | 5.965 | 8.176 | 5.965 | 8.914 | −0.671 | 0.067 |
| | Rep 2 | | 6.702 | 5.227 | 5.227 | 8.176 | 8.176 | 9.651 |
| | Rep 3 | | 7.439 | 5.965 | 7.439 | 0.067 | 7.439 | 6.702 |
| Normalisation | Rep 1 | | 34.659 | 64.517 | 26.535 | 32.377 | 23.091 | −308.186 |
| | Rep 2 | | 39.572 | 90.048 | 68.313 | 43.061 | 111.107 | 50.159 |
| | Rep 3 | | 26.441 | 92.923 | 98.311 | 118.804 | 70.911 | 58.020 |
| | Mean | | 33.557 | 82.496 | 64.387 | 37.719 | 91.009 | 54.089 |
| | Standard deviation | | 6.634 | 15.636 | 36.049 | 7.555 | 28.423 | 5.559 |

The results show that there is more Osteogenic activity where the coupons have been chemically treated e.g. with an alkaline solution compared to not being chemically treated.

It will be appreciated that the primary layer may include various bio-active materials including antimicrobials. It will also be appreciated that the primary layer may be further treated to impart anti-biofouling, cytogenic, catalytic, osteogenic or electrochemical properties to the implant.

It will be further appreciated that the substrate may comprise other metals or alloys instead of titanium, for example, nitinol or zirconium.

It is envisaged that the material formed maybe subjected to further physical treatment steps to improve or enhance the surface characteristics of the primary surface layer. For example, on completion of the primary layer, the material can be rinsed in water or phosphate buffered saline solution to remove the alkali. After drying the material, it can be heated to a target temperature of between 300-600° C. The target temperature can be reached by raising the temperature of the material by 5° C. per minute. The target temperature, once reached can be maintained for at least one hour.

It will be appreciated that the invention is not limited to the embodiments hereinbefore described but may be varied in construction and detail within the scope of the appended claims.

The invention claimed is:

1. A material suitable as an implant comprising:
   (a) a titanium or titanium alloy substrate comprising a first surface having a first surface area;
   (b) a plurality of metallic beads adhered to the first surface, wherein the plurality of metallic beads are micron scale structures that collectively form a second surface having a second surface area that is greater than the first surface area, and (c) a surface layer on the plurality of metallic beads comprising alkali titanates, wherein the surface layer has a thickness between 100 and 300 nanometers, and wherein the surface layer comprises a plurality of nanoscale structures that collectively form a third surface comprising a third surface area that is greater than the second surface area.

2. The material of claim 1, wherein the micron scale structures comprises a double or triple layer of metallic beads.

3. The material of claim 1, wherein the metallic beads are sintered onto the surface of the substrate.

4. The material of claim 1, wherein the metallic beads comprise titanium.

5. The material of claim 1, wherein the metallic beads have a mean diameter of 328 micrometers.

6. The material of claim 1, wherein the metallic beads have diameters between 15 and 50 micrometers.

7. The material of claim 1, wherein the surface layer further comprises titanium oxide.

8. The material of claim 1, wherein the third surface area is between 1000 and 50,000 times greater than the first surface area.

9. The material of claim 1, wherein the plurality of nanoscale structures comprises discrete fibrils of alkali titanate comprising a width in the range of 1 to 20 nanometers.

10. The material of claim 1, wherein the plurality of micron scale structures and the surface layer together are a primary layer on the substrate, wherein the primary layer covers the first surface.

11. The material of claim 10, wherein the primary layer further comprises hydroxyapatite.

12. A material suitable as an implant comprising:
(a) a titanium or titanium alloy substrate comprising a first surface having a first surface area;
(b) a plurality of metallic fibers adhered to the first surface, wherein the plurality of metallic fibers are micron scale structures that collectively form a second surface having a second surface area that is greater than the first surface area, and
(c) a surface layer on the plurality of metallic fibers comprising alkali titanates, wherein the surface layer has a thickness between 100 and 300 nanometers, and wherein the surface layer comprises a plurality of nanoscale structures that collectively form a third surface comprising a third surface area that is greater than the second surface area;
wherein the plurality of micron scale structures and the surface layer together are a primary layer on the substrate,
wherein the primary layer covers the first surface, and
wherein the primary layer further comprises hydroxyapatite.

* * * * *